(12) United States Patent
Kleven

(10) Patent No.: US 8,800,373 B2
(45) Date of Patent: Aug. 12, 2014

(54) ACOUSTIC TRANSDUCER ASSEMBLY FOR A PRESSURE VESSEL

(75) Inventor: Lowell A. Kleven, Eden Prairie, MN (US)

(73) Assignee: Rosemount Inc., Eden Prairie, MN (US)

(*) Notice: Subject to any disclaimer, the term of this patent is extended or adjusted under 35 U.S.C. 154(b) by 203 days.

(21) Appl. No.: 13/026,790

(22) Filed: Feb. 14, 2011

(65) Prior Publication Data

US 2012/0204650 A1    Aug. 16, 2012

(51) Int. Cl.
  *G01N 29/28*    (2006.01)

(52) U.S. Cl.
  USPC .................................. 73/644; 73/622; 73/46

(58) Field of Classification Search
  CPC ............ G01N 19/2462; G01N 29/329; G01N 2291/2695; F16T 1/48
  USPC ....................... 73/587, 592, 622, 638, 644, 46
  See application file for complete search history.

(56) References Cited

U.S. PATENT DOCUMENTS

| | | | | |
|---|---|---|---|---|
| 3,107,950 A | | 10/1963 | Kleven | 308/36 |
| 4,570,489 A | * | 2/1986 | Baumaire et al. | 73/658 |
| 4,898,022 A | * | 2/1990 | Yumoto et al. | 73/46 |
| 4,945,343 A | * | 7/1990 | Rodriguez | 340/606 |
| 5,065,785 A | | 11/1991 | Deacon et al. | 137/185 |
| 5,353,628 A | * | 10/1994 | Bellows | 73/25.01 |
| 5,625,150 A | * | 4/1997 | Greene et al. | 73/649 |
| 5,992,436 A | | 11/1999 | Hellman et al. | 137/1 |
| 6,047,602 A | * | 4/2000 | Lynnworth | 73/632 |
| 6,145,529 A | | 11/2000 | Hellman et al. | 137/1 |
| 6,220,098 B1 | * | 4/2001 | Johnson et al. | 73/592 |
| 6,234,021 B1 | | 5/2001 | Piety et al. | 73/592 |
| 6,338,283 B1 | * | 1/2002 | Blazquez Navarro et al. | 73/865.8 |
| 6,675,665 B2 | * | 1/2004 | Blazquez Navarro et al. | 73/865.8 |
| 7,203,626 B2 | | 4/2007 | Quake et al. | 702/178 |
| 7,246,036 B2 | | 7/2007 | Cheskaty et al. | 702/183 |
| 7,664,610 B2 | * | 2/2010 | Anderson et al. | 702/51 |
| 7,703,326 B2 | | 4/2010 | Puttmer | 73/587 |
| 7,912,675 B2 | * | 3/2011 | Quake et al. | 702/182 |
| 7,913,566 B2 | * | 3/2011 | Hedtke | 73/649 |
| 7,956,738 B2 | * | 6/2011 | Karschnia et al. | 340/538 |
| 8,050,875 B2 | * | 11/2011 | Karschnia | 702/51 |
| 8,188,359 B2 | * | 5/2012 | Chakraborty | 136/205 |
| 8,250,924 B2 | * | 8/2012 | Hedtke | 73/660 |
| 2006/0118648 A1 | | 6/2006 | Armstrong et al. | 236/93 |
| 2007/0073495 A1 | | 3/2007 | Anderson et al. | 702/50 |

FOREIGN PATENT DOCUMENTS

| | | |
|---|---|---|
| CA | 1287903 | 8/1991 |
| CN | 1010344 B | 11/1990 |
| EP | 0 097 100 | 6/1983 |
| EP | 0 697 595 | 2/1996 |

(Continued)

OTHER PUBLICATIONS

Search Report and Written Opinion from PCT/US2012/024101, dated Jun. 28, 2012.

(Continued)

*Primary Examiner* — Peter Macchiarolo
*Assistant Examiner* — Samir M Shah
(74) *Attorney, Agent, or Firm* — Westman, Champlin & Koehler, P.A.

(57) ABSTRACT

A transducer assembly includes an acoustic sensor element and an acoustic waveguide. The acoustic waveguide includes a rotatable acoustic coupler, a tube, and a foot. The foot has a mounting surface that is mountable on a fluid conduit. A circuit assembly couples to acoustic sensor element and provides a diagnostic output.

29 Claims, 15 Drawing Sheets

(56) References Cited

FOREIGN PATENT DOCUMENTS

| | | |
|---|---|---|
| EP | 0 949 447 | 10/1999 |
| EP | 0 949 447 A1 | 10/1999 |
| GB | 2 457 924 | 9/2009 |

OTHER PUBLICATIONS

Communication pursuant to Rules 161(1) and 162 EPC for European Patent Application No. 12706741.1, dated Sep. 20, 2013, 2 pages.
Office Action from CN 201110303825.7, dated Mar. 26, 2014.

* cited by examiner

ACOUSTIC TRANSDUCER ASSEMBLY FOR A PRESSURE VESSEL

BACKGROUND

The present application relates to the monitoring of pressure vessels. More particularly, the present application relates to transducing malfunctions in flow control such as leaky valves, stuck valves, liquid or gas phases, or multiple phases associated with flow control in pressure vessels.

Steam traps are commonly used in many industries to remove condensate from steam lines. In a typical plant, thousands of such devices may be deployed. A steam trap is generally a relatively low technology device that is designed to be relatively inexpensive. Often, steam traps are completely mechanical. Adding any electrical wiring for either powering or wiring would be considered cost prohibitive, impractical or labor intensive.

A steam trap is generally designed to allow condensate to escape a steam pipe in order to maintain efficiency and prevent pipe "knocking". A typical steam trap may have one or more chambers and a movable member that is in physical contact with the condensate. As the level of condensate rises above some threshold, the movable member within the steam trap actuates or otherwise engages one or more valves to allow at least some of the condensate to escape. As the condensate escapes, the level of condensate within the steam trap is reduced to such an extent that the valve is closed.

Malfunctioning steam traps can leak steam which wastes energy or can fail to remove condensate properly. In many instances, the malfunction is not detected by plant control systems and is therefore unknown to plant personnel for extended periods of time.

Other types of flow control devices associated with pressure vessels such as control valves, orifices, nozzles and restrictions are subject to malfunctions.

SUMMARY

A transducer assembly includes an acoustic sensor element and an acoustic waveguide. The acoustic waveguide includes a tube that has a first tube end acoustically coupled to the acoustic sensing element by a rotatable acoustic coupler. The acoustic waveguide further includes a second tube end. The second tube end has a mounting surface that is mountable on a fluid conduit. A circuit assembly is coupled to the acoustic sensor element and provides a diagnostic output that identifies a steam leak based upon a received acoustic signal. A method is also included.

DETAILED DESCRIPTION

In the embodiments described below, a transducer assembly detects malfunctions in flow control such as leaking gasses in pressure vessels such as valves, steam traps, flow restrictors, pressure relief valves and the like. The transducer assembly uses acoustic sensing. In some embodiments, temperature sensing is used as well. In one example, when there is a low level of noise or no acoustic noise detected, and a pressure vessel temperature is near saturation temperature of the steam, then a steam trap is operating normally. When acoustic noise rises above a threshold level and the temperature is near the saturation temperature of the steam, then the transducer assembly senses and indicates that a valve in the pressure vessel is leaking. When the acoustic noise is high and temperature is low, then the transducer assembly senses and indicates that a valve in the pressure vessel is in a start-up condition with air leaking. When there is no acoustic noise and the temperature is low, then the transducer assembly senses and indicates that a valve in the pressure vessel is plugged, jammed or not operational. The invention, however, is not limited to this exemplary diagnostic technique.

The transducer assembly includes an acoustic sensor element and an acoustic waveguide. The acoustic waveguide allows the diagnostic circuitry to be thermally separated from a high temperature vessel. The acoustic waveguide includes a rotatable acoustic coupler, such as a spring or shaft for example, that couples to the acoustic sensor, and includes a tube that couples to the rotatable acoustic coupler and to a foot that has a mounting surface that mounts to a fluid conduit connected to the pressure vessel. In one embodiment, a temperature sensor senses temperature in an internal thermowell cavity in the foot and has an output cable that extends through the tube. A thermowell cavity is a protected cavity in a thermowell. A thermowell is a protecting tube designed to enclose a temperature sensing device in a cavity and protect the temperature sensing device from deleterious effects of the environment. According to one embodiment, an electronics assembly in the transducer assembly receives temperature and acoustic noise data from the sensors and provides a wireless output that couples to a remote monitor.

Figure 1:
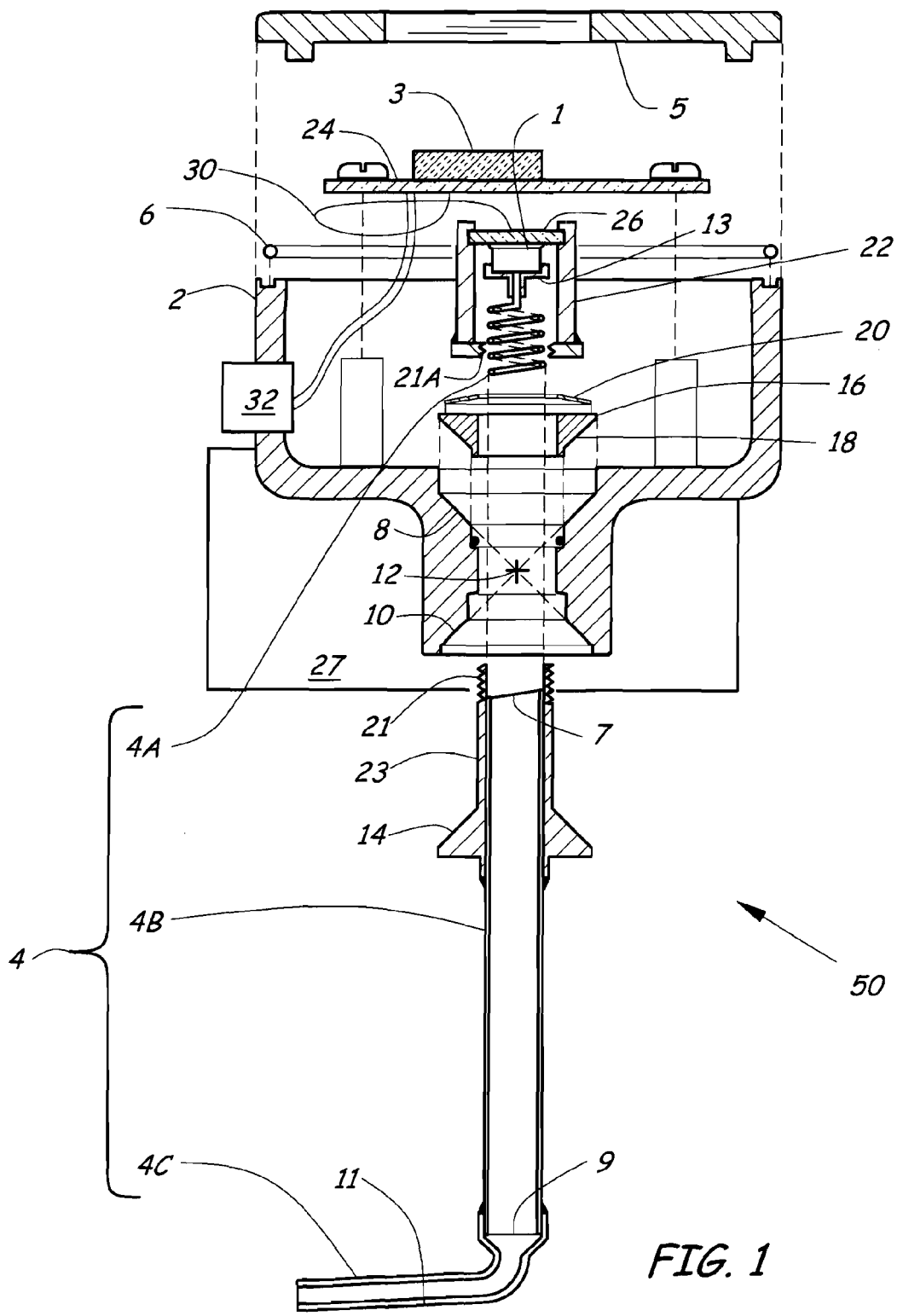
FIG. 1 illustrates a first embodiment of a transducer assembly.

FIG. 1 illustrates an exploded view of a transducer assembly 50. The transducer assembly 50 includes an acoustic sensor element 1. According to one embodiment, the acoustic sensor element 1 includes a piezoelectric force sensor. According to another embodiment, the acoustic sensor element 1 includes a capacitive force sensor. According to yet another embodiment, the acoustic sensor element 1 includes a magnetic force sensor.

The transducer assembly 50 includes an acoustic waveguide 4. The acoustic waveguide 4 includes a spring 4A that rotatably couples to the acoustic sensor element 1. The acoustic waveguide 4 includes a tube 4B that has a first tube end 7 coupled to the spring 4A.

The acoustic waveguide 4 includes a foot 4C which provides a coupling region that couples to a second tube end 9 of the tube 4B. The foot 4C includes a mounting surface 11 that is mountable in contact with a fluid conduit (not illustrated in FIG. 1).

The acoustic waveguide 4 couples an acoustic vibration from the mounting surface 11 of the foot 4C to the acoustic sensor element 1. It will be understood by those skilled in the arts that the tube 4B and the foot 4C can be formed of a single tube, and in that case there is no joint between the tube 4B and the foot 4C. According to one embodiment, acoustic vibration is sensed in the range of 30 kHz to 50 kHz.

According to one embodiment, the tube 4B has a length that spaces the acoustic sensor element 1 a distance away from the foot 4C to provide thermal isolation. High temperature at the foot 4C, which is typically clamped to a line on a process vessel, is attenuated along the length of the tube 4B such that the acoustic sensor element 1 has a lower temperature that is near the temperature of the surrounding ambient air. The tube 4B is hollow, as illustrated, which reduces thermal conduction along the length of the tube 4B.

According to one embodiment, the spring 4A is positioned adjacent the acoustic sensor element 1 by an insulating cap 13 that provides a rotatable joint between the spring 4A and the acoustic sensor element 1. The insulating cap 13 couples the acoustic vibration from the spring 4A to the acoustic sensor element 1. The insulating cap 13 positions the spring 4A in a position where it exerts a force on the acoustic sensor element 1.

According to one embodiment, the insulating cap 13 is formed of electrically insulating material and is dimensioned to provide adequate electrical clearance and creepage distances between the sensor element 1 and the electrically conducting spring 4A to ensure electrical isolation. According to another embodiment, the spring 4A is at a pipe electrical potential, and the sensor element 1 is at an electronic circuit potential, and the insulating cap 13 provides galvanic isolation to ensure that intrinsic safety requirements are met for circuitry in the transducer assembly 50.

According to one embodiment, the transducer assembly 50 includes an electronic housing mounting flange 23 that is mounted to the tube 4B and that includes a threaded flange portion 21 adjacent the first tube end 7. In this embodiment, the electronic housing mounting flange 23 is used to mount an electronic housing 2 adjacent the first tube end 7. According to another embodiment, the transducer assembly 50 includes a sensor support adapter 22. The sensor support adapter 22 includes a printed wiring board 26 that slides into slots of the adapter 22 for mounting. In this embodiment, the acoustic sensor element 1 is mounted on the printed wiring board for mechanical support and electrical connection. The sensor support adapter 22 is threaded with threads 21A that engage the threads 21. As thread engagement progresses, the spring 4A exerts an increasing force on the acoustic sensor element 1 and compresses the spring 4A, eliminating free play or lost motion in the acoustic waveguide 4.

Electrical leads 30 of the acoustic sensor element 1 provide an acoustic energy output that is electrical and that couples to electronics. The acoustic energy output on electrical leads 30 is useful for diagnostic testing of steam traps and other process fluid vessels.

According to one embodiment, the tube 4B includes a metal tube having an external diameter of less than 11 millimeters. According to another embodiment, the tube 4B includes a tube wall thickness of less than 2.0 millimeter.

The transducer assembly 50 includes the electronic housing 2 and a housing cover 5. An O-ring 6 provides a seal between the electronics housing 2 and the cover 5.

The electronic housing 2 includes frustoconical inner surfaces 8, 10 that have a conic apex 12 that is common to both frustoconical inner surfaces 8, 10. A frustoconical outer surface 14 of the electronic housing mounting flange 23 is assembled adjacent the frustoconical inner surface 10. The transducer assembly 50 includes a frustoconical washer 16 that has a frustoconical outer surface 18 that is assembled adjacent the frustoconical inner surface 8. A spring washer (also called a Belleville washer) 20 is positioned on top of the frustoconical washer 16. The threads 21A of the sensor support adapter 22 are threaded onto threads 21 of the electronic housing mounting flange 23, compressing the spring washer 20. The arrangement of the frustoconical surfaces 8, 10, 14, 18 having a common apex 12 provides a connection between the housing 2 and the flange 23 that maintains stable spacing even though the housing 2 and tube 4B are formed of materials with different temperature coefficients of expansion.

An electronics assembly 24 provides wireless communication through the cover 5. A battery 27 energizes the electronics assembly 24. The electronics assembly 24 includes stored thresholds of acoustic signal level. The stored thresholds are stored in non-volatile memory and are adjustable by wireless communication. The real time levels of acoustic signal level are compared to the respective stored thresholds in order to perform diagnostic decision making in real time. The electronics assembly 50 also includes a stored identification number or name that is transmitted wirelessly to identify the source of the data or diagnostic decision.

According to one embodiment, the housing 2 supports an electrical connector 32 for connection to an external temperature sensor (not illustrated in FIG. 1). In this embodiment, the electronics assembly 24 makes decisions based on both acoustic signal level and also an external temperature. According to another embodiment, the electronics assembly includes a digital display 3 that is visible through a window in the cover 5.

Figure 2:
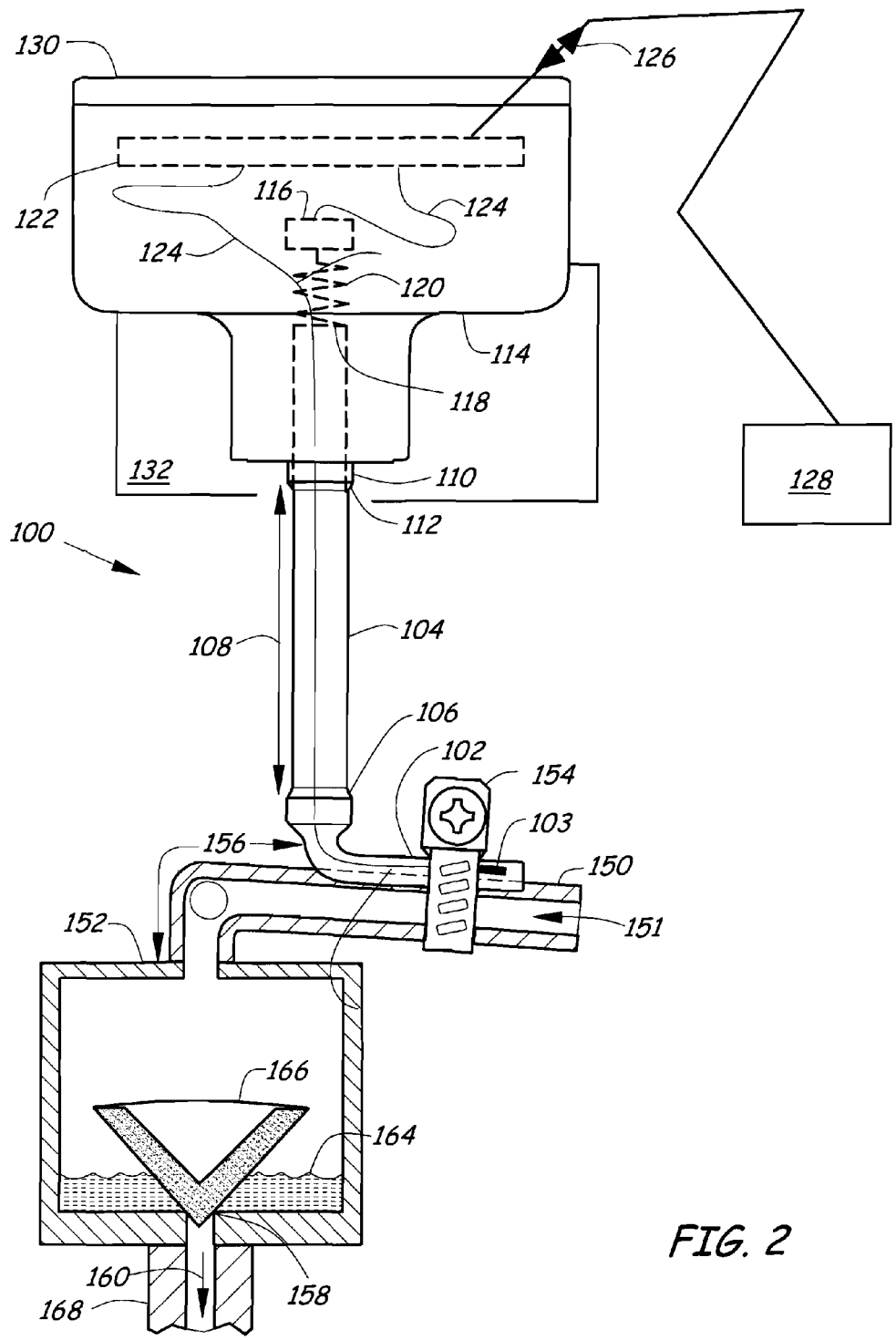
FIG. 2 illustrates a second embodiment of a transducer assembly mounted adjacent a steam trap.

FIG. 2 illustrates a transducer assembly 100 that is secured to a steam/condensate line 150 that brings a condensate/steam mixture 151 to a steam trap 152. One or more clamps 154 secure a foot 102 of the transducer assembly 100 to the steam/condensate line 150. The clamp or clamps 154 can be hose clamps, locking pliers, C-clamps or other known types of clamps. As illustrated in FIG. 2, the foot 102 has a concave rounded surface that is clamped in contact with a convex round outer surface of the steam/condensate line 150.

A piping length 156 between the foot 102 and the steam trap 152 is kept short so that a temperature at the foot 102 is representative of a temperature of the condensate/steam mixture 151. A condensate 160 is separated from the steam and is discharged from the steam trap 152. A temperature sensor 103 is enclosed inside the foot 102 in a thermowell cavity. The piping length 156 is sufficiently short that acoustic noise generated by a fluid flow through a valve 158 in the steam trap 152 readily couples with low attenuation along the steam/condensate line 150 from the valve 158 to the foot 102. The foot 102 of the transducer assembly 100 is in thermal and acoustic communication with the steam trap 152 for transducing performance of the steam trap 156 and for diagnostic testing of the steam trap 156 such as detection of leaks, plugging and a start-up condition.

The steam trap 152 couples to the steam/condensate line 150. According to one embodiment, the steam/condensate line 150 carries steam from a steam source (not illustrated in FIG. 2) to a steam utilization device (not illustrated in FIG. 2). Condensate in the steam/condensate line 150 drains into the steam trap 152. Stored condensate 164 accumulates inside the steam trap 152 until a sufficient amount of stored condensate 164 has accumulated to raise a float 166 and open the valve 158. When the valve 158 opens, condensate 164 flows into drain line 168 (as indicated by arrow 160) until the float 166 sinks and closes the valve 158 with some stored condensate 164 still present in the steam trap 152. The arrangement of the float 166, valve 158, and stored condensate 164 traps steam in the steam trap 152, while allowing excess condensate to drain. When functioning properly, the steam trap 152 performs the useful function of draining off undesired excess condensate in the steam/condensate line 150, while preventing loss of steam (and an associated loss of energy) through the steam trap 152. When the steam trap 152 malfunctions, there can be a great loss of energy, plugging of the steam/condensate line 150 with condensate, or other problems.

The foot 102 of the transducer assembly 100 is attached to a tube 104 by a weld 106. The tube 104 has a tube length 108. The tube 104 is welded to an electronic housing mounting flange 110 by a weld 112. According to one embodiment, the tube 104 has a round cylindrical cross section as illustrated. According to another aspect the tube 104 has a generally rectangular cross section. The electronic housing mounting flange 110 supports an electronic housing 114. The electronic housing 114 encloses an acoustic sensor element 116. The acoustic sensor element 116 is acoustically coupled to an end 118 of the pipe 104 by a spring 120. An electronics assembly 122 couples by leads 124 to the acoustic sensor element 116 and the temperature sensor 103. The electronics assembly 122 communicates using wireless communication signals 126 with, for example, a remote monitoring station 128. A housing cover 130 is transparent to the wireless communication signals 126. According to one embodiment, the housing cover 130 includes thermoplastic resin. A battery 132 energizes the electronics assembly 122.

The foot 102, the tube 104 and the spring 120 function as an acoustic waveguide that couples acoustic vibration or an acoustic signal from a mounting surface on steam/condensate line 150 (at foot 102) to the acoustic sensor element 116. According to one embodiment, the acoustic vibrations sensed by the acoustic sensor element 116 are in a range of 30 kHz to 50 kHz. The acoustic vibrations originate in the steam trap 152, particularly at the valve 158 due to gas flow through the valve 158. The gas flow through valve 158 can be steam in the case of a leaky valve, and can be either air or steam in the case of a start-up condition. The electronics assembly 122 processes acoustic and temperature data from the sensors 103, 116 to calculate diagnostic information concerning the function of the steam trap 156. According to one embodiment, the foot 102, the clamp 154 and the steam/condensate line 150 are wrapped in thermal insulation at the time of installation to reduce a temperature difference between the steam trap 152 and the temperature sensor 103. The operation of the transducer assembly 100 is described in more detail below by way of an example illustrated in FIG. 3.

Figure 3:
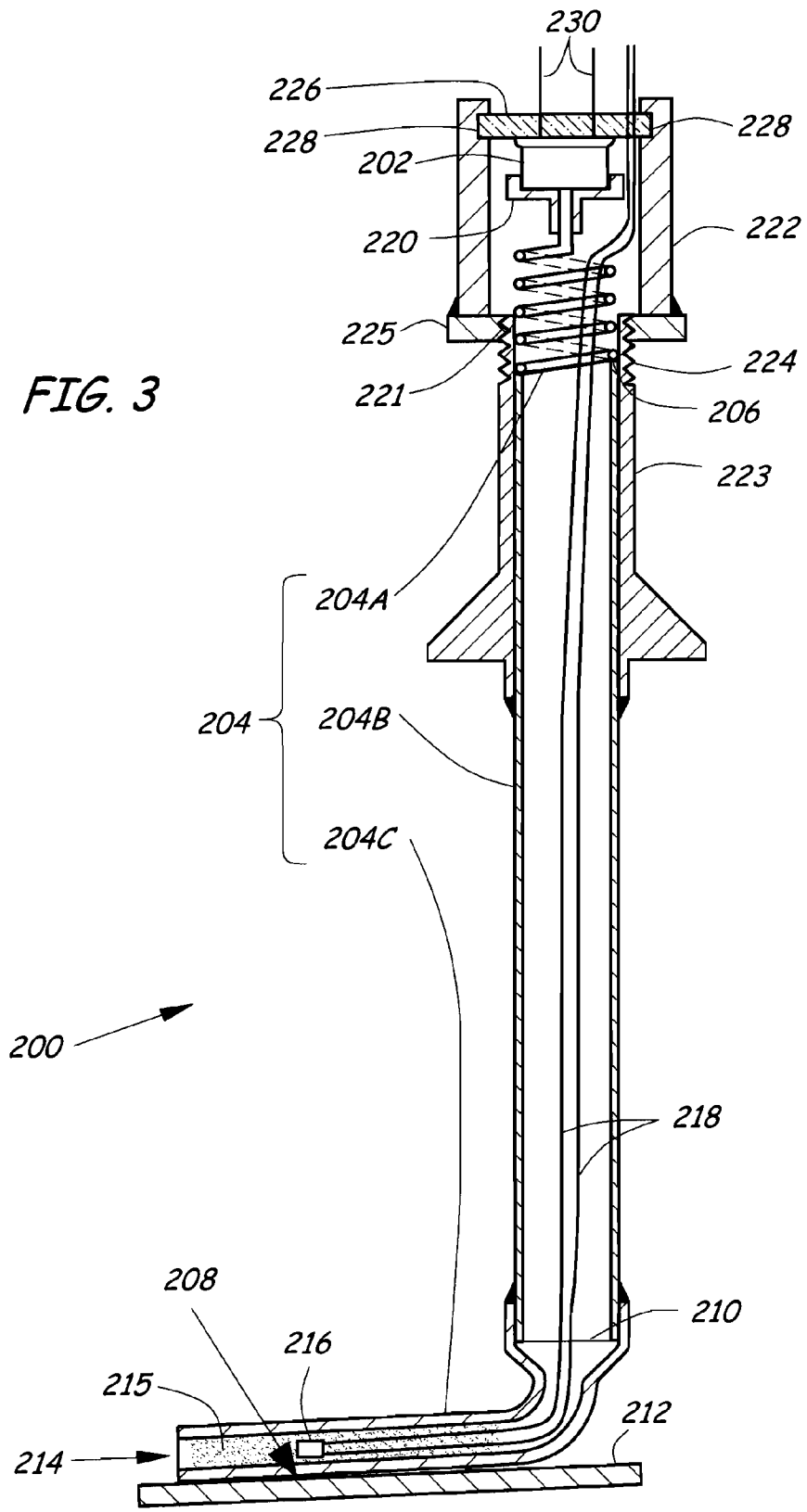
FIG. 3 illustrates a third embodiment of a transducer assembly.

FIG. 3 illustrates a transducer assembly 200. The transducer assembly 200 includes an acoustic sensor element 202. According to one embodiment, the acoustic sensor element 202 includes a piezoelectric force sensor. According to another embodiment, the acoustic sensor element 202 includes a capacitive force sensor. According to yet another embodiment, the acoustic sensor element 202 includes a magnetic force sensor.

The transducer assembly 202 includes an acoustic waveguide 204. The acoustic waveguide 204 includes a spring 204A that rotatably couples to the acoustic sensor element 202. The acoustic waveguide 204 includes a tube 204B that has a first tube end 206 coupled to the spring 204A.

The acoustic waveguide 204 includes a foot 204C which provides a coupling region that couples to a second tube end 210 of the tube 204B. The foot 204C includes a mounting surface 208 that is mountable in contact with a fluid conduit 212. The foot 204C includes an internal thermowell cavity 214 adjacent the mounting surface 208. A temperature sensor 216 is disposed in the thermowell cavity 214 and senses a temperature in the internal thermowell cavity 214. Space in the thermowell cavity 214 can be filled with a quantity of heat conducting potting compound 215. According to one embodiment, the potting compound 215 includes a thin layer of inorganic ceramic cement for high temperatures sold by Sauereisen Cements Company of Pittsburgh, Pa. 15238 USA. The heat conducting compound 215 provides good thermal coupling between the temperature sensor 216 and the fluid conduit 212. The temperature sensor 216 connects to an output cable 218 that extends through the tube 204B and the first tube end 206. According to one embodiment, the temperature sensor 216 includes a thermistor. According to another embodiment, the temperature sensor 216 includes a thermocouple junction.

The acoustic waveguide 204 couples an acoustic vibration from the mounting surface 208 of the foot 204C to the acoustic sensor element 202. It will be understood by those skilled in the arts that the tube 204B and the foot 204C can be formed of a single tube, and in that case there is no joint between the tube 204B and the foot 204C. According to one embodiment, the acoustic vibration is sensed in the range of 30 kHz to 50 kHz.

According to one embodiment, the tube 204B has a length that spaces the acoustic sensor element 202 a distance away from the foot 204C to provide thermal isolation. High temperature at the foot 204C, which is typically clamped to a steam trap drain line, is attenuated along the length of the tube 204B such that the acoustic sensor element 202 has a lower temperature that is near the temperature of the surrounding ambient air. The tube 204B is hollow, as illustrated, which reduces thermal conduction along the length of the tube 204B.

According to one embodiment, the spring 204A is positioned adjacent the acoustic sensor element 202 by an insulating cap 220 that provides a rotatable joint between the spring 204A and the acoustic sensor element 202. The insulating cap 220 couples the acoustic vibration from the spring 204A to the acoustic sensor element 202. The insulating cap 220 positions the spring 204A in a position where it exerts a force on the acoustic sensor element 202. According to one embodiment, the insulating cap 220 is formed of electrically insulating material and is dimensioned to provide adequate electrical clearance and creepage distances between the sensor element 202 and the electrically conducting and spring 204 to ensure electrical isolation. According to another embodiment, the spring 204A is at a pipe electrical potential, and the sensor element 202 is at an electronic circuit potential, and the insulating cap 220 provides galvanic isolation to ensure that intrinsic safety requirements are met for circuitry in the transducer assembly 200.

According to one embodiment, the transducer assembly 200 includes an electronic housing mounting flange 223 that is mounted to the tube 204B and that includes a threaded flange portion 224 adjacent the first tube end 206. In this embodiment, the electronic housing mounting flange 223 is used to mount an electronic housing (not illustrated in FIG. 3) adjacent the first tube end 206.

According to another embodiment, the transducer assembly 200 includes a sensor support adapter 222. The sensor support adapter 222 includes a printed wiring board 226 that slides into slots 228 of the adapter 222 for mounting. In this embodiment, the acoustic sensor element 202 is mounted on the printed wiring board for mechanical support and electrical connection. The sensor support adapter 222 is threaded with threads 221 that engage the threaded flange portion 224.

Electrical leads 230 of the acoustic sensor element 202 and the output cable 218 of the temperature sensor 216 provide acoustic energy and temperature outputs and couple to electronics (not illustrated in FIG. 3). The temperature and acoustic energy outputs are useful for diagnostic testing of steam traps and other process fluid vessels. The sensor support adapter 222 includes a threaded support end 225 with the threads 221 that engage the threaded flange portion 224. As thread engagement progresses, the spring 204A exerts an increasing force on the acoustic sensor element 202 and compresses the spring 204A, eliminating free play or lost motion in the acoustic waveguide 204.

According to one embodiment, the tube 204B includes a metal tube having an external diameter of less than 11 millimeters. According to another embodiment, the tube 204B includes a tube wall thickness of less than 2.0 millimeter. The assembly and operation of the transducer assembly 200 is described in more detail below in connection with an example illustrated in FIG. 4.

Figure 4:
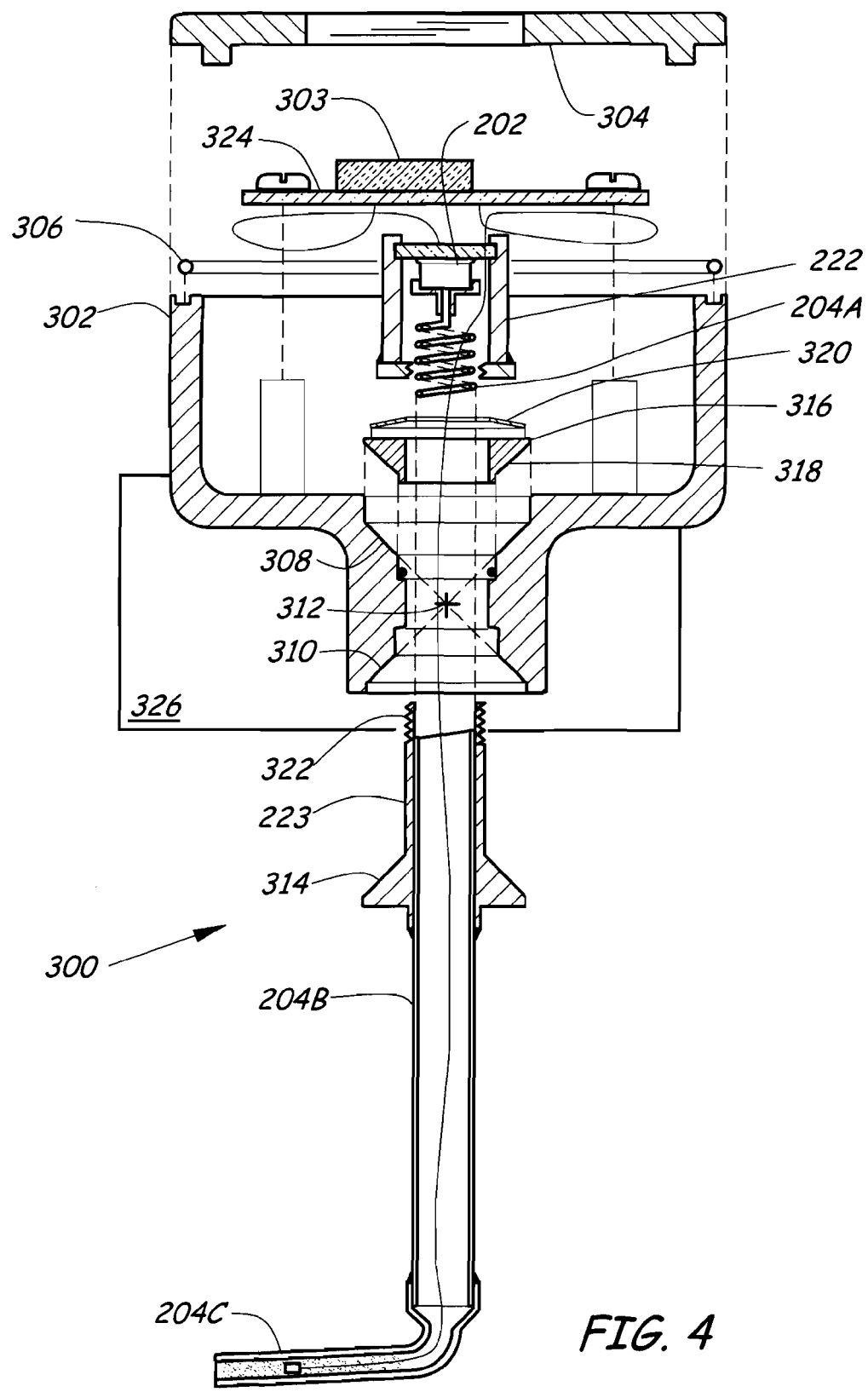
FIG. 4 illustrates a fourth embodiment of a transducer assembly.

FIG. 4 illustrates an exploded view of a transducer assembly 300. The transducer assembly 300 includes a waveguide that includes a spring 204A, a tube 204B and a foot 204C as illustrated in FIG. 3. The transducer assembly 300 includes an acoustic sensor element 202, a sensor support adapter 222, and an electronic housing mounting flange 223 as illustrated in FIG. 3. Reference can be made to FIG. 3 and the description of FIG. 3 for a description of the assembly and function of components that are common to FIG. 3 and FIG. 4. The transducer assembly 300 includes an electronic housing 302 and a housing cover 304. An O-ring 306 provides a seal between the electronics housing 302 and the cover 304.

The electronic housing 302 includes frustoconical inner surfaces 308, 310 that have a conic apex 312 that is common to both frustoconical inner surfaces 308, 310. A frustoconical outer surface 314 of the electronic housing mounting flange 223 is assembled adjacent the frustoconical inner surface 310. The transducer assembly 300 includes a frustoconical washer 316 that has a frustoconical outer surface 318 that is assembled adjacent the frustoconical inner surface 308. A spring washer (also called a Belleville washer) 320 is positioned on top of the frustoconical washer 316. The sensor support adapter 222 is threaded onto threads 322 of the electronic housing mounting flange 223, compressing the spring washer 320. The arrangement of the frustoconical surfaces 308, 310, 314, 318 having a common apex 312 provides a connection between the housing 302 and the flange 223 that maintains stable spacing even though the housing 302 and tube 204B are formed of materials with different temperature coefficients of expansion.

An electronics assembly 324 provides wireless communication through the cover 304. In other respects, the transducer assembly 300 is similar to the transducer assembly 100 in FIG. 2. A battery 326 energizes the electronics assembly 324. The electronics assembly 324 includes stored thresholds of temperature and acoustic signal level. The stored thresholds are stored in non-volatile memory and are adjustable by wireless communication. The real time levels of temperature and acoustic signal level are compared to the respective stored thresholds in order to perform diagnostic decision making real time temperate and level data, decision, or both are transmitted by wireless communication. The electronics assembly 324 also includes a stored identification number or name that is transmitted wirelessly to identify the source of the data or diagnostic decision. The electronics assembly 324 includes a digital display 303 that is visible through a window in the cover 304.

Figure 5A:
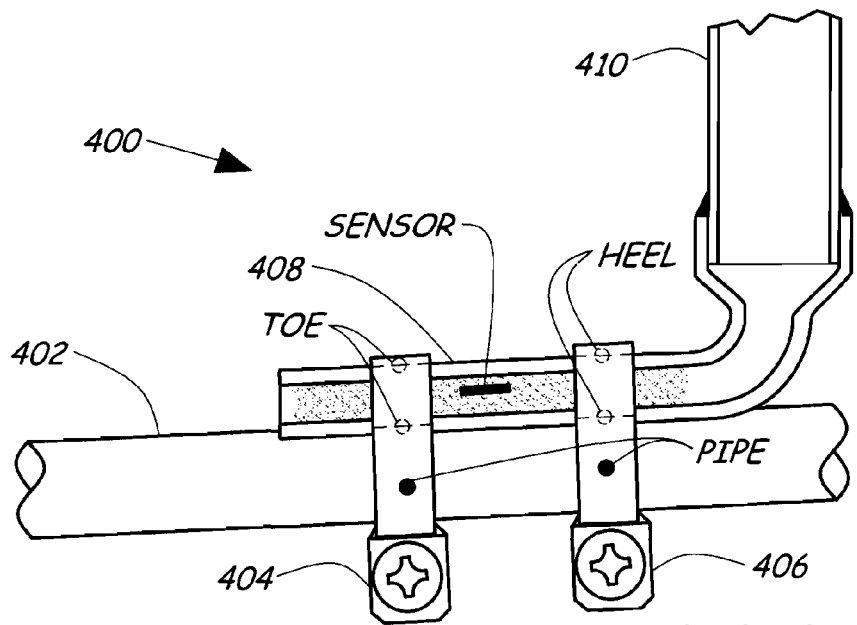
FIG. 5A illustrates temperature sensing locations on a transducer assembly.

FIG. 5A illustrates temperature sensing locations on a transducer assembly 400. The transducer assembly 400 includes a foot 408 secured to a condensate drain pipe 402 by clamps 404, 406. During normal operation, the condensate drain pipe 402 carries heated condensate. Heat flows from the condensate drain pipe 402 through the transducer assembly 400 to the surrounding ambient, which is at a lower temperature. There is therefore a temperature gradient in the transducer assembly 400. The temperature gradient is beneficial in that it provides a lower operating temperature for an electronics assembly (such as assembly 122 in FIG. 2). The temperature gradient is problematic in that it becomes difficult to find a location on the transducer assembly 400 where a temperature sensor can be located to obtain a temperature reading from which a temperature of the condensate drain pipe can be inferred accurately.

For purposes of measuring temperatures during a design test, thermocouple junctions are compressed under the clamp 404 at locations indicated by TOE near a toe end of the foot 408. Thermocouple junctions are compressed under the clamp 406 at locations indicated by HEEL at a heel end of the foot 408.

Figure 5B:
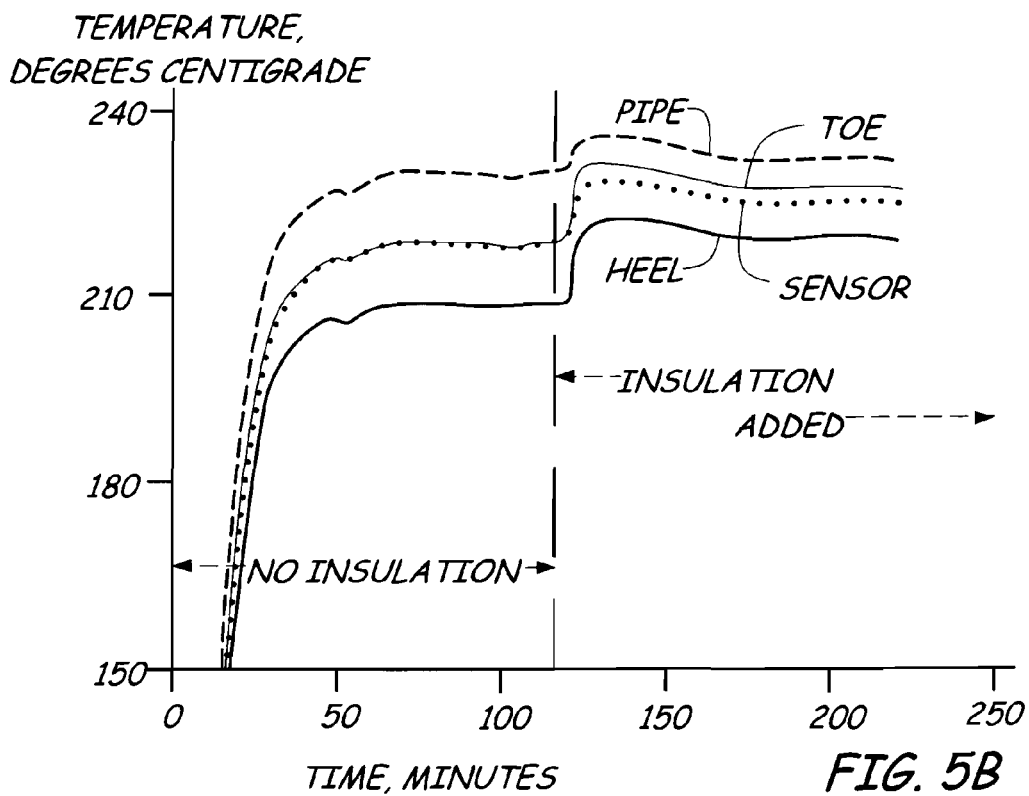
FIG. 5B illustrates a graph of temperatures for the temperature sensing locations of FIG. 5A.

Readings from the thermocouple junctions under the toe clamp 404 are averaged to provide a recorded TOE temperature reading as illustrated in FIG. 5B. Readings from the thermocouple junctions under the heel clamp 406 are averaged to provide a recorded HEEL temperature reading as illustrated in FIG. 5B.

Two thermocouple junctions are attached to the condensate drain pipe 402 at locations indicated by PIPE. Readings from the thermocouple junctions at the pipe locations are averaged to provide a PIPE temperature reading as indicated in FIG. 5B. A SENSOR which is part of the transducer assembly 400 provides a SENSOR temperature reading in FIG. 5B.

FIG. 5B illustrates a graph of temperatures for the temperature sensing locations of FIG. 5A during a design test. As illustrated in FIG. 5B, the condensate drain pipe is heated starting at time zero. After approximately 100 minutes from time zero, recorded temperatures stabilize. After approximate 115 minutes from time zero, the foot 408 and the adjacent portion of the condensate drain pipe 402 are wrapped with thermal insulation. After approximately 200 minutes from time zero, recorded temperatures again stabilize. It can be seen by inspection of FIG. 5B, that the temperature recorded at location TOE is closest to the PIPE temperature. Based on the these results, the temperature sensor (such as temperature sensor 216 in FIG. 3) which is used in the transducer assembly 400 is advantageously placed near a TOE end of a foot 408 in order to provide improved accuracy of temperature reading. Based on these test results, thermal insulation can be wrapped around the foot 408 and adjacent condensate drain pipe 402 to reduce a temperature difference between the PIPE and the SENSOR, improving temperature measurement accuracy as illustrated in FIG. 5B.

According to one embodiment, temperature errors that remain in the temperature reading of the sensor are corrected electronically as described in more detail below in connection with FIG. 9.

Figure 6:
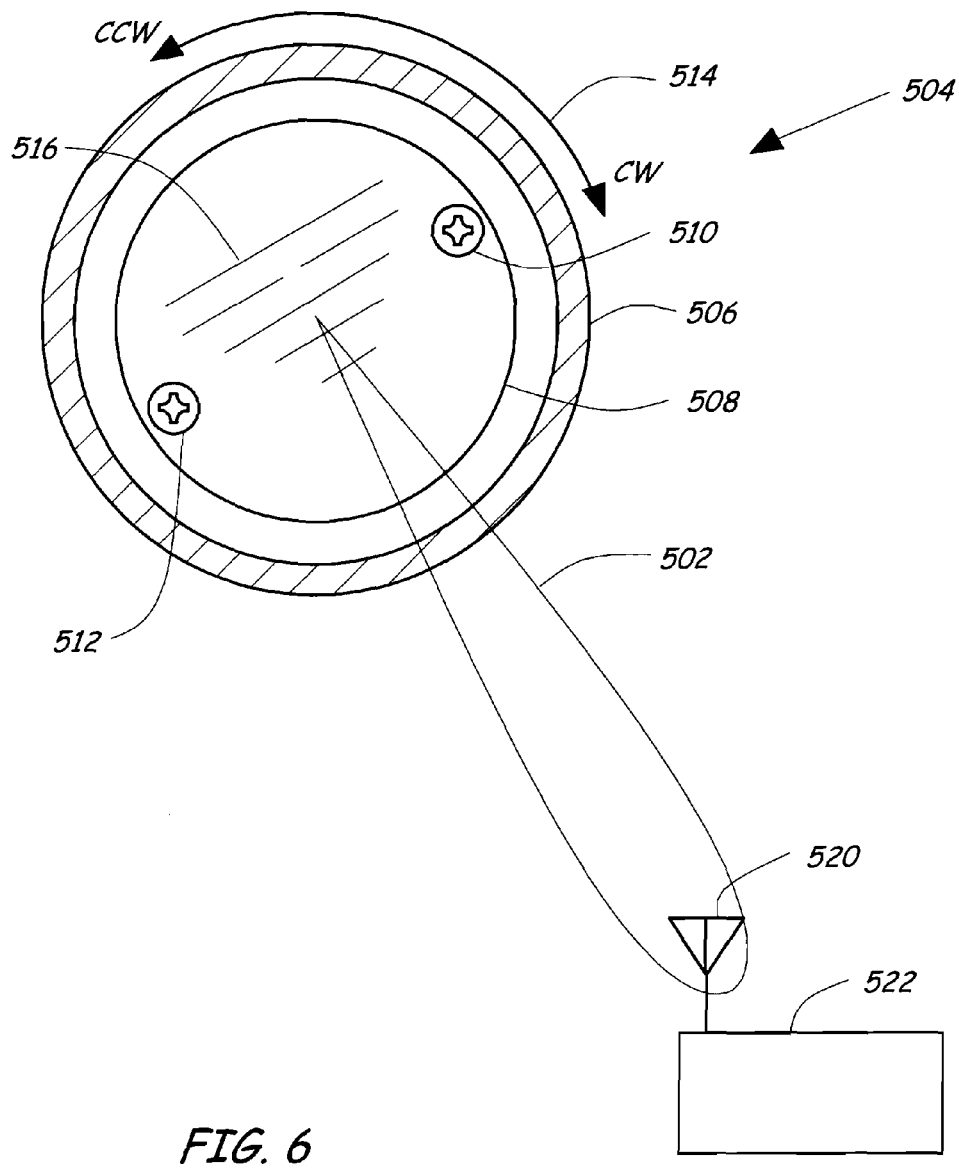
FIG. 6 illustrates a rotation of a main antenna lobe of a transducer assembly.

FIG. 6 illustrates a rotation of a main antenna lobe 502 of a transducer assembly 504. The transducer assembly 504 includes an electronics housing 506 (similar to electronics housing 302 in FIG. 4) and an electronics assembly 508 (similar to electronics assembly 324 in FIG. 4). The electronics assembly 508 is mounted to the electronics housing 508 by mounting screws 510, 512. The electronics housing 506 (and the attached electronics assembly 508) are rotatable as indicated by arrow 514. A directional antenna 516 on the electronics assembly 508 produces the main antenna lobe 502. That directional antenna 516 can also produce less salient antenna lobes. Rotation of the electronic housing 506 rotates the main antennal lobe 502, allowing an operator to aim the main antenna lobe 502 toward an antenna 520 of a remote monitoring station 522.

As illustrated above in FIG. 4, an electronic housing 302 is rotatable on frustoconical bearing surfaces 314, 318. A spring washer 320 provides a compressive force to the frustoconical bearing surfaces 314, 318. According to one embodiment, an electronic data display 303 is mounted to the electronics assembly 324. The rotatable frustoconical bearing surfaces 314, 318 are rotatable to orient the electronic data display 303 in a preferred direction for convenient reading by field service personnel. The rotatability of the display 303 overcomes a problem in which an electronic data display in a fixed position may by installed so that the electronic data display is not oriented for convenient reading.

Normally, the tube 204B (FIGS. 3-4) is installed in a horizontal orientation to avoid heat from a steam trap convecting toward the electronics. The electronic data display 303 mounted on the circuit board can be oriented for proper reading by rotating the electronics housing 302. According to one aspect, the electronic data display 303 is oriented on the electronics assembly 324 in relationship to an antenna on the electronics assembly 324 so that the antenna is preferentially oriented for transmission and reception when the display 303 is properly oriented for reading. Typically, the display 303 is oriented to read from left to right horizontally for reading of English letters and numbers by service personnel.

Figure 7A:
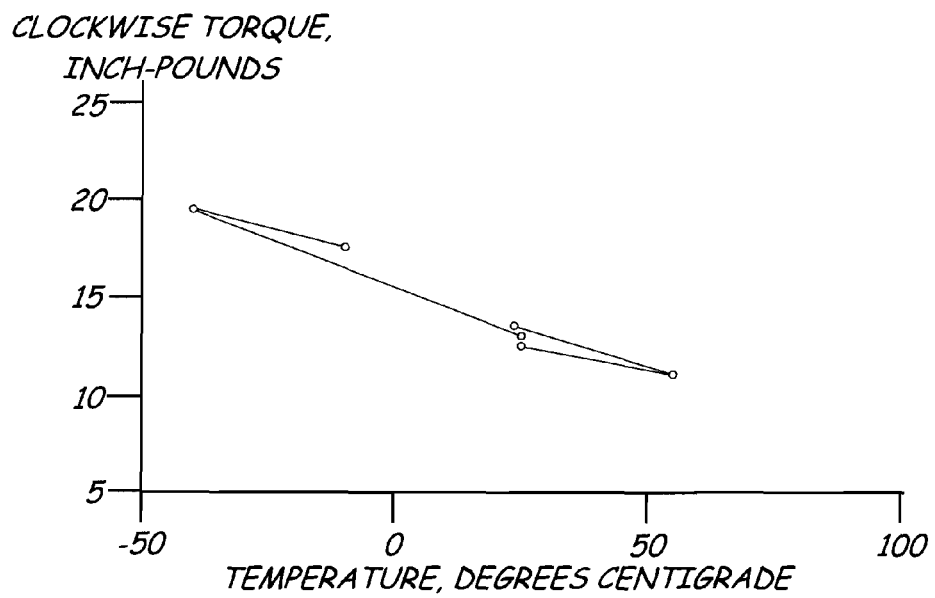
FIGS. 7A and 7B illustrate torque as a function of temperature for rotation of a main antenna lobe.
Figure 7B:
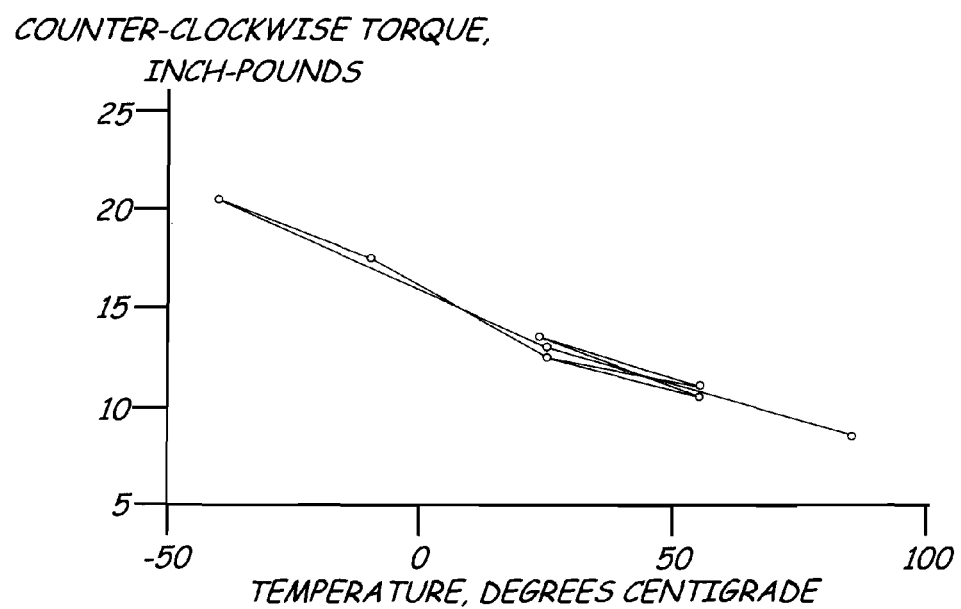

FIGS. 7A and 7B illustrate torque required for rotation as a function of temperature for rotation of the main antenna lobe 502. The torque is controlled by the compressive force of the spring washer 320 to provide torques in the range of 8 to 22 foot pounds. According to one aspect, the adjustable, controlled compressive force provided by the spring washer 320 in combination with the use of frustoconical bearing surfaces 308, 310, 314, 316 as rotational sliding surfaces provides for a desired controlled torque that is also adjustable. The torque range (in both clockwise and counterclockwise directions) is sufficiently high that vibration will not change the direction of the main antenna lobe 502. The torque range is sufficiently low (in both clockwise and counterclockwise directions) that the main antenna lobe 502 can be easily rotated by hand. The torque range is sufficiently stable over a temperature range of −40 degrees Centigrade to +80 degrees Centigrade because of the use of frustoconical bearing surfaces 308, 310 and the spring washer 320.

Figure 8:
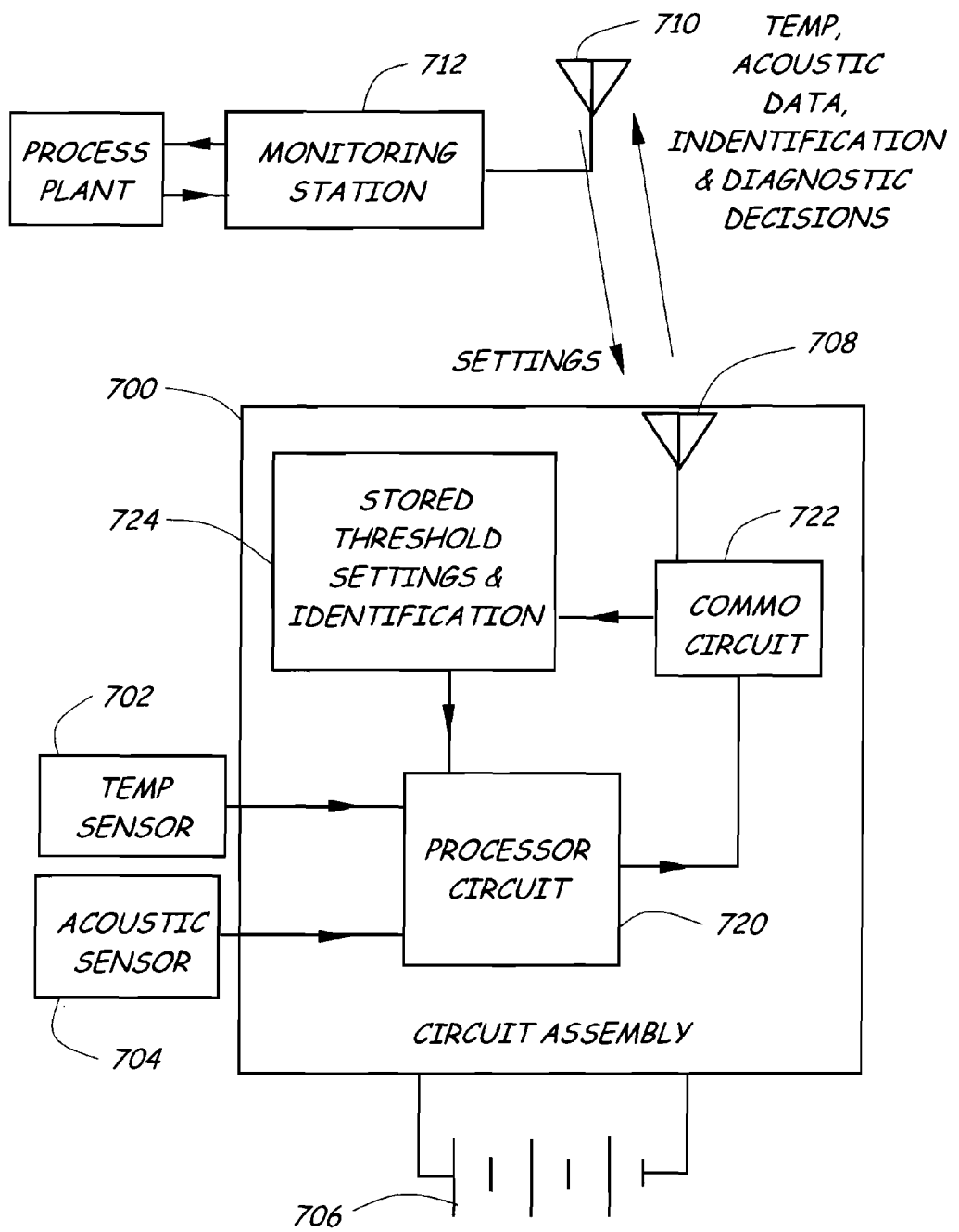
FIG. 8 illustrates a circuit assembly in a transducer assembly.

FIG. 8 illustrates a circuit assembly 700 for use in a transducer assembly such as transducer assembly 300 in FIG. 4 or transducer assembly 50 in FIG. 1. The circuit assembly 700 couples to a temperature sensor 702 which provides temperature data, and to an acoustic sensor element 704 that provides acoustic data. According to one embodiment illustrated in FIG. 1, the temperature sensor 704 is external. According to another embodiment illustrated in FIG. 3, the temperature sensor 704 is part of the transducer assembly. The circuit assembly 700 couples to a battery 706 that energizes the circuit assembly 700.

The circuit assembly 700 includes an antenna 708 for communication with an antenna 710 that couples to a monitoring station 712. According to one aspect, the antenna 708 comprises a directional antenna. According to another aspect, the antenna 708 comprises a pattern of printed conductors on a printed circuit board.

The circuit assembly comprises a processor circuit 720. According to one aspect, the processor circuit 720 makes decisions as described in more detail below in connection with a logic flow chart in FIG. 9. The processor circuit provides decision outputs to a communication circuit 722. The communication circuit 722 encodes the decisions and stored identification data according to a standard communication protocol and transmits the decisions and identification data using the antenna 708.

Threshold settings for decision making and an identification number for the circuit assembly 700 are stored in a non-volatile storage circuit 724. According to one aspect, the non-volatile storage circuit 724 comprises EEPROM memory. As part of commissioning or startup operations, the monitoring station 712 transmits threshold setting to the circuit assembly 700 for storage in the non-volatile storage circuit 724.

Figure 9:
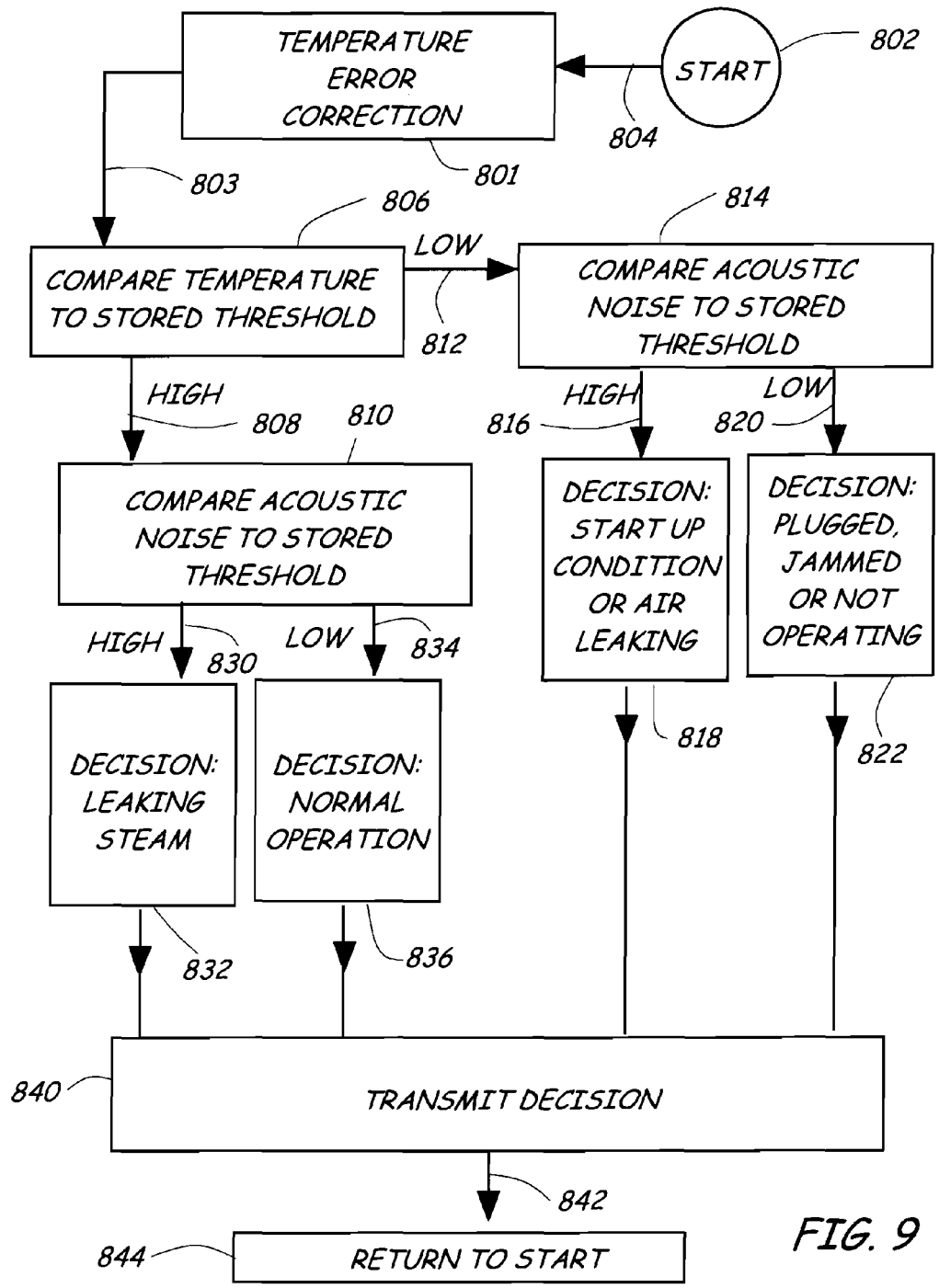
FIG. 9 illustrates a diagnostic flow chart.

FIG. 9 illustrates a diagnostic flow chart that illustrates an example of decisions that can be performed by the processor circuit 720 of FIG. 8. Processing begins at START 802 and continues along a line 804 to an action block 801. At action block 801, an optional temperature error correction algorithm is performed. After optional completion of the temperature error correction algorithm, processing continues along line 803 to decision block 806.

According to one embodiment, the temperature error correction algorithm in the action block 801 performs a static error correction routine:

$$T_{PC} = T_W + (K \times (T_W - T_C))$$

where:
$T_{PC}$ represents a corrected pipe temperature;
$T_W$ represents a sensor temperature;
$T_C$ represents a circuit board temperature; and
K represents a static correction coefficient determined by tests.

According to another embodiment, the temperature error correction algorithm in the action block 801 performs a dynamic error correction routine:

$$T_{PC} = T_W + (K \times (T_W - T_C)) + M \times \frac{d(T_W - T_C)}{dt}$$

where:
$T_{PC}$ represents a corrected pipe temperature;
$T_W$ represents a sensor temperature;
$T_C$ represents a circuit board temperature;
K represents a static correction coefficient determined by tests;
M represents a dynamic correction coefficient determined by tests; and
d/dt represents mathematical differentiation.

At decision block 806, temperature data is compared to a stored temperature threshold. If the temperature is higher than the stored temperature threshold, then processing continues along line 808 to a decision block 810. If the temperature is lower than the stored temperature threshold, then processing continues along line 812 to decision block 814.

At decision block 814, if acoustic noise is higher than a stored acoustic noise threshold, then processing continues along line 816 to an action block 818. At action block 818, a decision is recorded that the monitored device is in a start up condition or leaking air. If acoustic noise is lower than the stored acoustic noise threshold, the processing continues along line 820 to an action block 822. At action block 822, a decision is recorded that the monitored device is jammed or not operating.

At decision block 810, if acoustic noise is higher than the stored acoustic noise threshold, then processing continues along line 830 to an action block 832. At action block 832, a decision is recorded that the monitored device is leaking steam. If acoustic noise is lower than the stored acoustic noise threshold, then processing continues along line 834 to an action block 836. At action block 836, a decision is recorded that the monitored device is in normal operation.

At action block 840, a most recent decision from one of actions blocks 818, 822, 832 or 836 is transmitted to a communication circuit for wireless transmission along with an identification number. After transmission, processing continues along line 842 to action block 844. At action block 844, decisions in blocks 832, 836, 818, 822 are reset, and processing returns to start 802.

Figure 10:
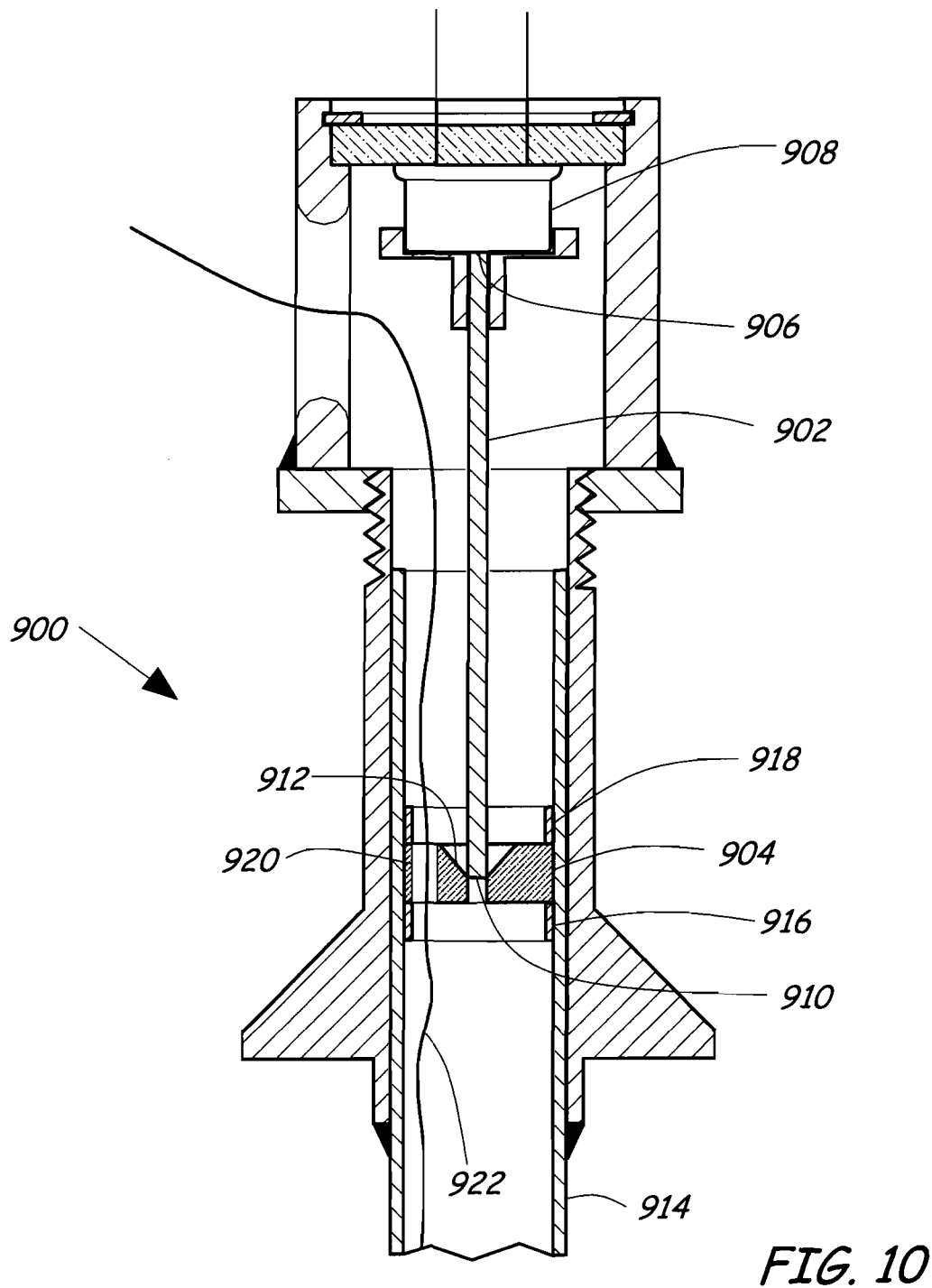
FIG. 10 illustrates an alternative embodiment of a rotatable acoustic coupler.

FIG. 10 illustrates an alternative embodiment of a rotatable acoustic coupler 900. The rotatable acoustic coupler 900 comprises a central shaft 902 and a socket 904. The central shaft 902 has a first shaft end 906 that is acoustically coupled to an acoustic sensor element 908. The central shaft 902 has a second shaft end 910 that is coupled to the socket 904. A length of the central shaft between the first shaft end 906 and the socket 904 is sufficiently long to permit flexing of the central shaft 902 to allow for small misalignments between the central shaft 902 and the socket 904. The socket 904 has a tapered opening 912 to allow for small misalignments.

According to one embodiment, the socket 904 is held in placed in a tube 914 by retainer rings 916, 918. According to another embodiment, the tapered opening 912 of the socket 904 tapers to an interference fit with the central shaft 902. The socket 904 contacts the central shaft 902 to provide acoustic coupling between the tube 914 and the central shaft 902. According to one aspect, the socket 904 is formed of an elastic material to provide contact. According to another aspect, the socket 904 is formed of heat-stabilized type 6 polyamide available from Professional Plastics Inc., Fullerton, Calif., USA 92831. The gripping joint between the central shaft 902 and the socket 904 is rotatable.

According to one aspect the socket 904 includes one or more radial openings 920 through which electrical leads 922 of a temperature sensor can be threaded.

Figure 11A:
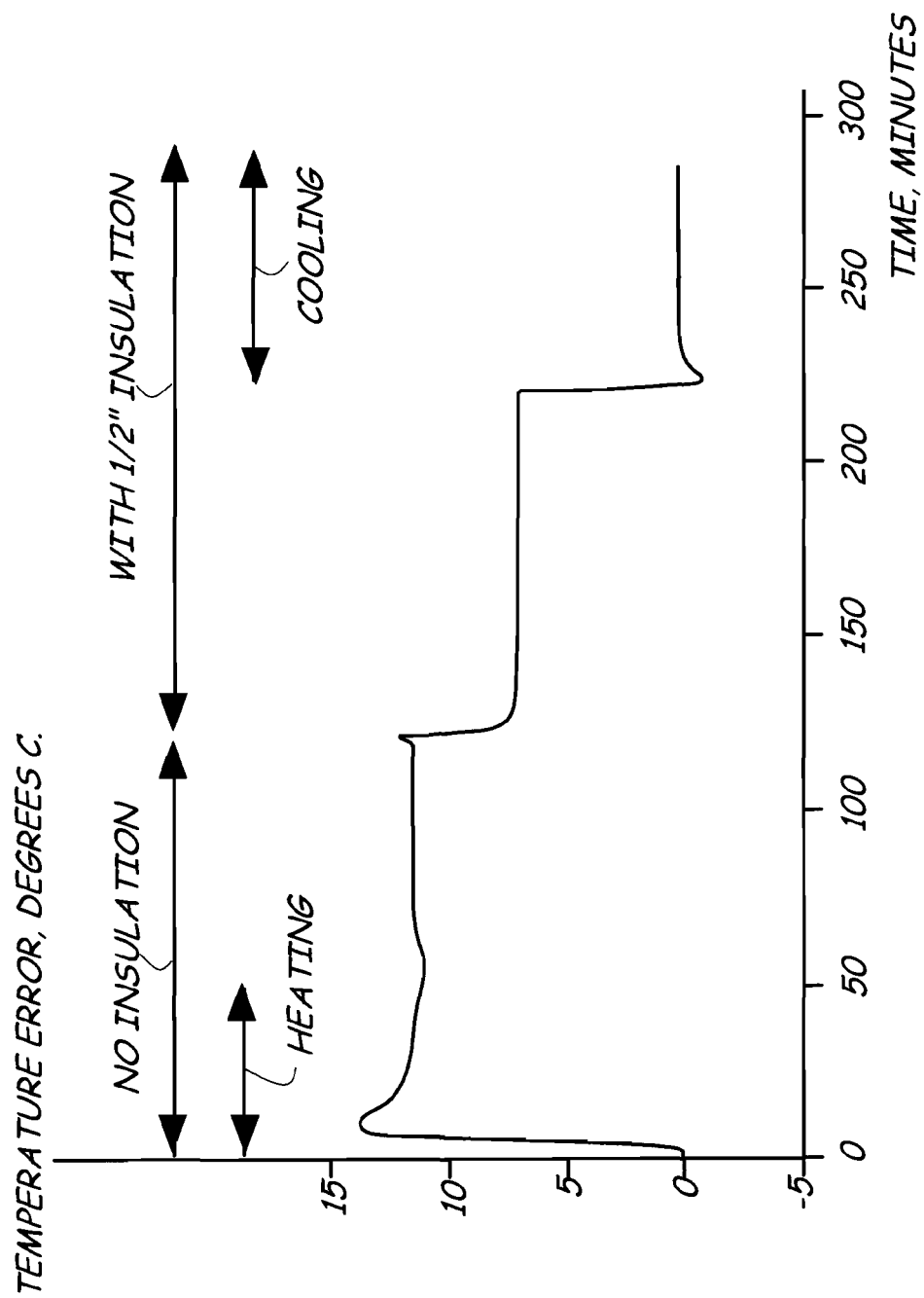
FIG. 11A illustrates a graph of temperature error without use of error correction routines.

FIG. 11A illustrates a graph of an exemplary temperature error without use of error correction routines. As shown in the graph in FIG. 11A, uncompensated static temperature errors are approximately 12 degrees Centigrade without the use of insulation, and approximately 7 degrees Centigrade with the use of insulation. Uncompensated dynamic temperature errors range up to approximately 14 degrees without the use of insulation and 7 degrees with the use of insulation.

Figure 11B:
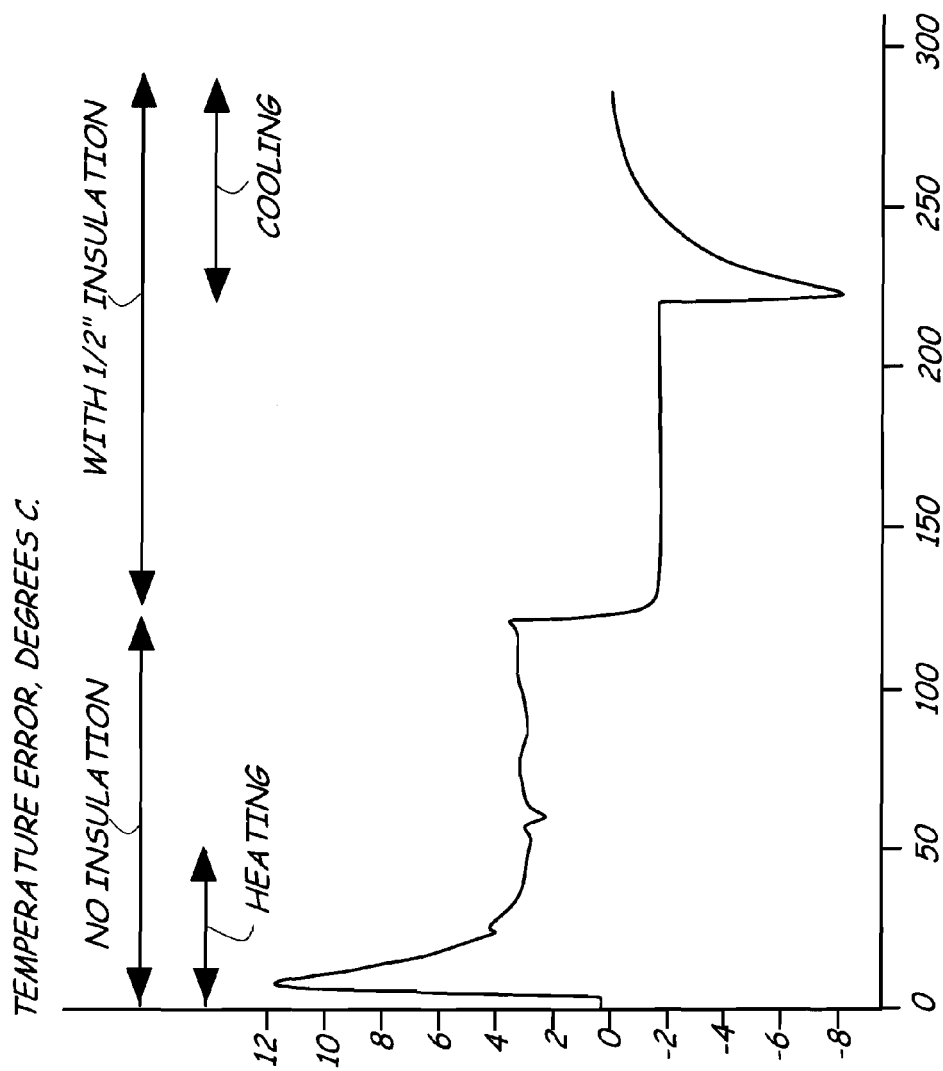
FIG. 11B illustrates a graph of temperature error using a static error correction routine.

FIG. 11B illustrates a graph of exemplary temperature error using a static error correction routine. As shown in the graph in FIG. 11B, static compensated static temperature errors are approximately 3 degrees Centigrade without the use of insulation and approximately −2 degrees Centigrade with the use of insulation. Static compensated dynamic temperature errors range up to approximately 12 degrees without the use of insulation and −2 degrees with the use of insulation.

Figure 11C:
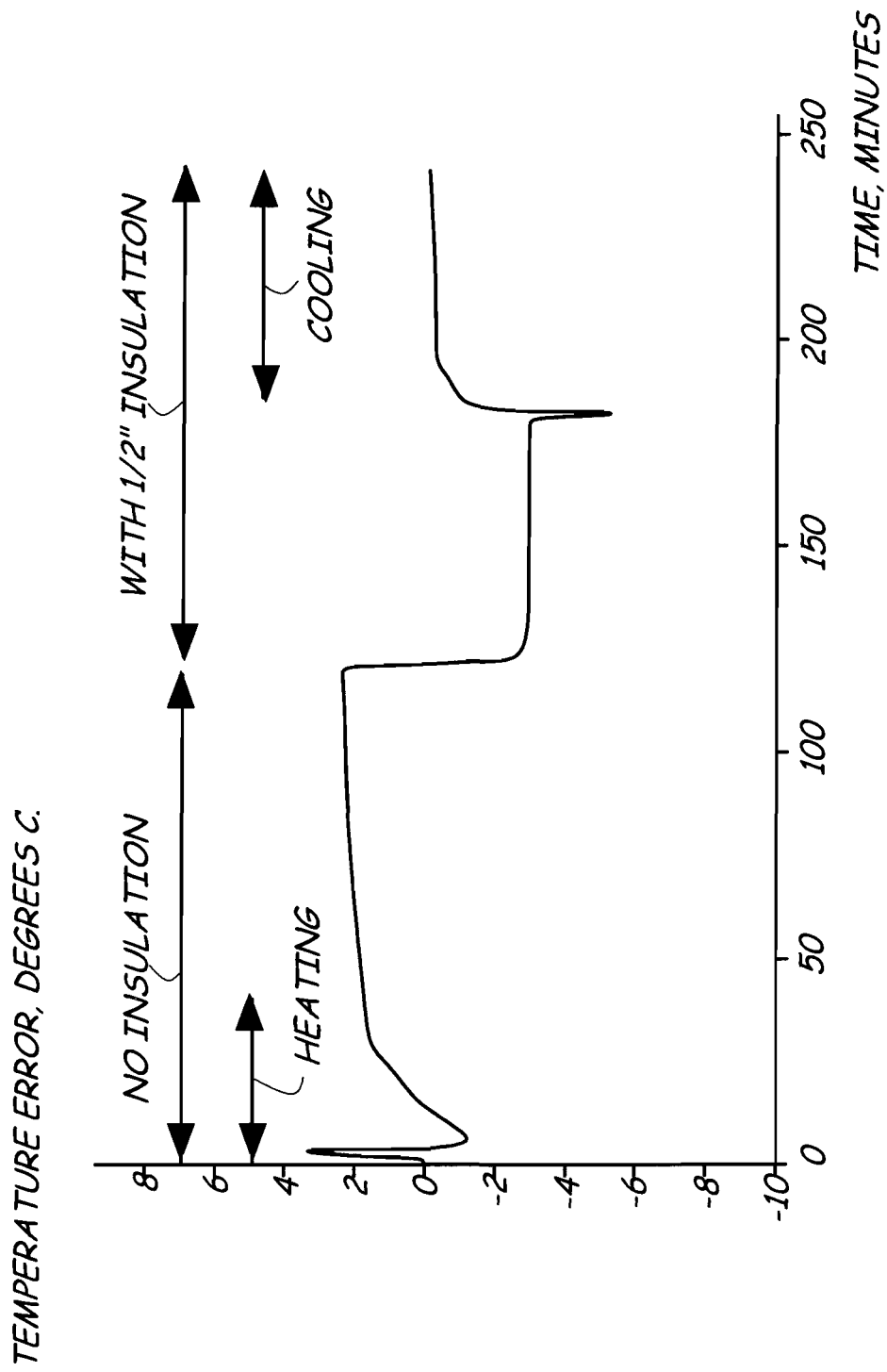
FIG. 11C illustrates a graph of temperature error using a dynamic error correction routine.

FIG. 11C illustrates a graph of temperature error using a dynamic error correction routine. As shown in the graph in FIG. 11C, dynamically compensated static temperature errors are approximately 2 degrees Centigrade without the use of insulation, and approximately −2.5 degrees Centigrade with the use of insulation. Dynamically compensated dynamic temperature errors range up to approximately −2 degrees without the use of insulation and −2.5 degrees with the use of insulation.

The data in FIGS. 11A, B, C illustrate that static and dynamic compensation can reduce temperature measurement error significantly. According to one aspect, the temperature compensation is adjustable by service personnel at the installation site to adapt to the use or lack of use of insulation in the installation.

Figure 12:
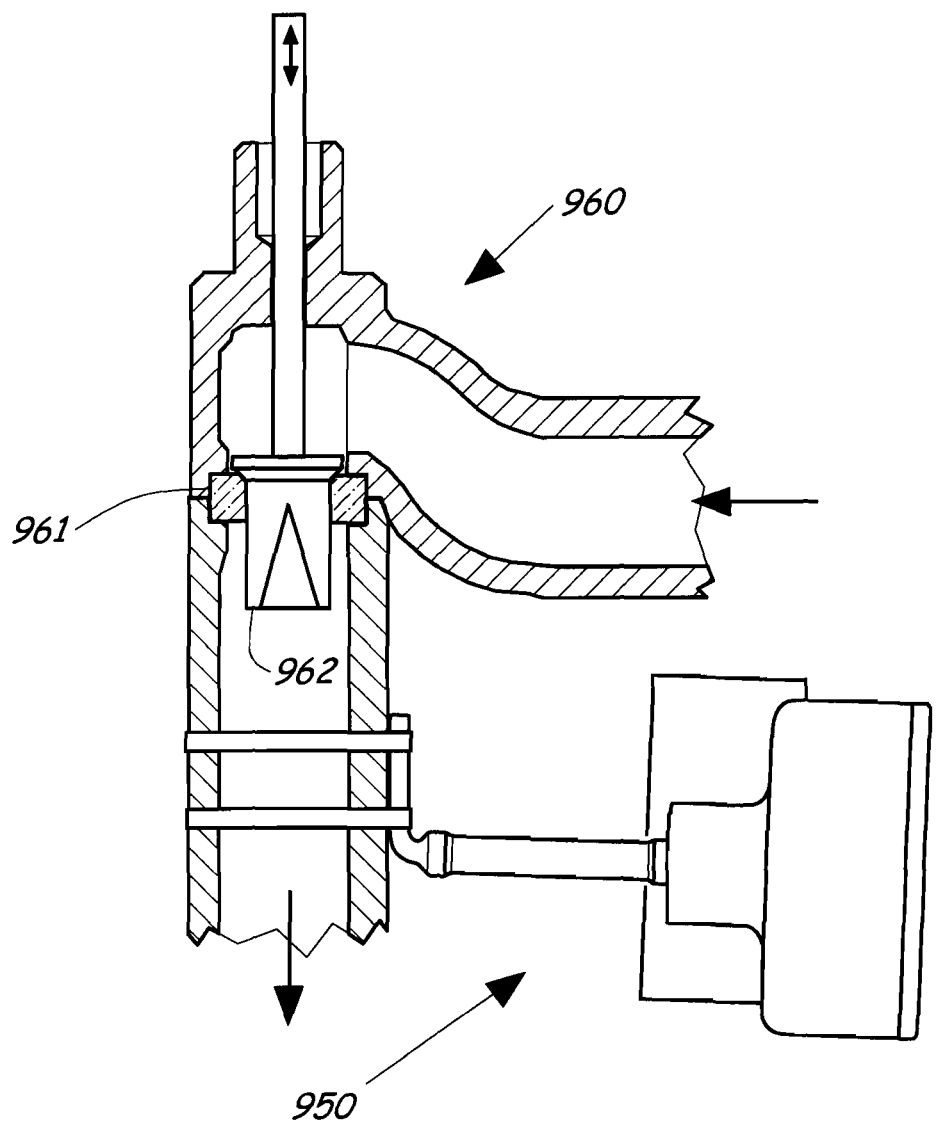
FIG. 12 illustrates a transducer assembly mounted to an actuatable control valve controlling a fluid flow.

FIG. 12 illustrates a transducer assembly 950 coupled to an outlet of an actuatable control valve 960. The control valve 960 includes a valve seat 961 and a valve plug 962 that is movable relative to the valve seat 961. According to one embodiment, when the control valve 960 is nominally closed, but there is leakage past the seal between the valve seat 961 and the valve plug 962, acoustic noise is generated by the leakage that is sensed and diagnosed by the transducer assembly 950. According to another embodiment, when control valve 960 operates normally with liquid flow, but the valve is instead filled with air, and air is flowing through the valve 960, acoustic noise is generated by the air flow and is sensed and diagnosed by the transducer assembly 950.

Figure 13:
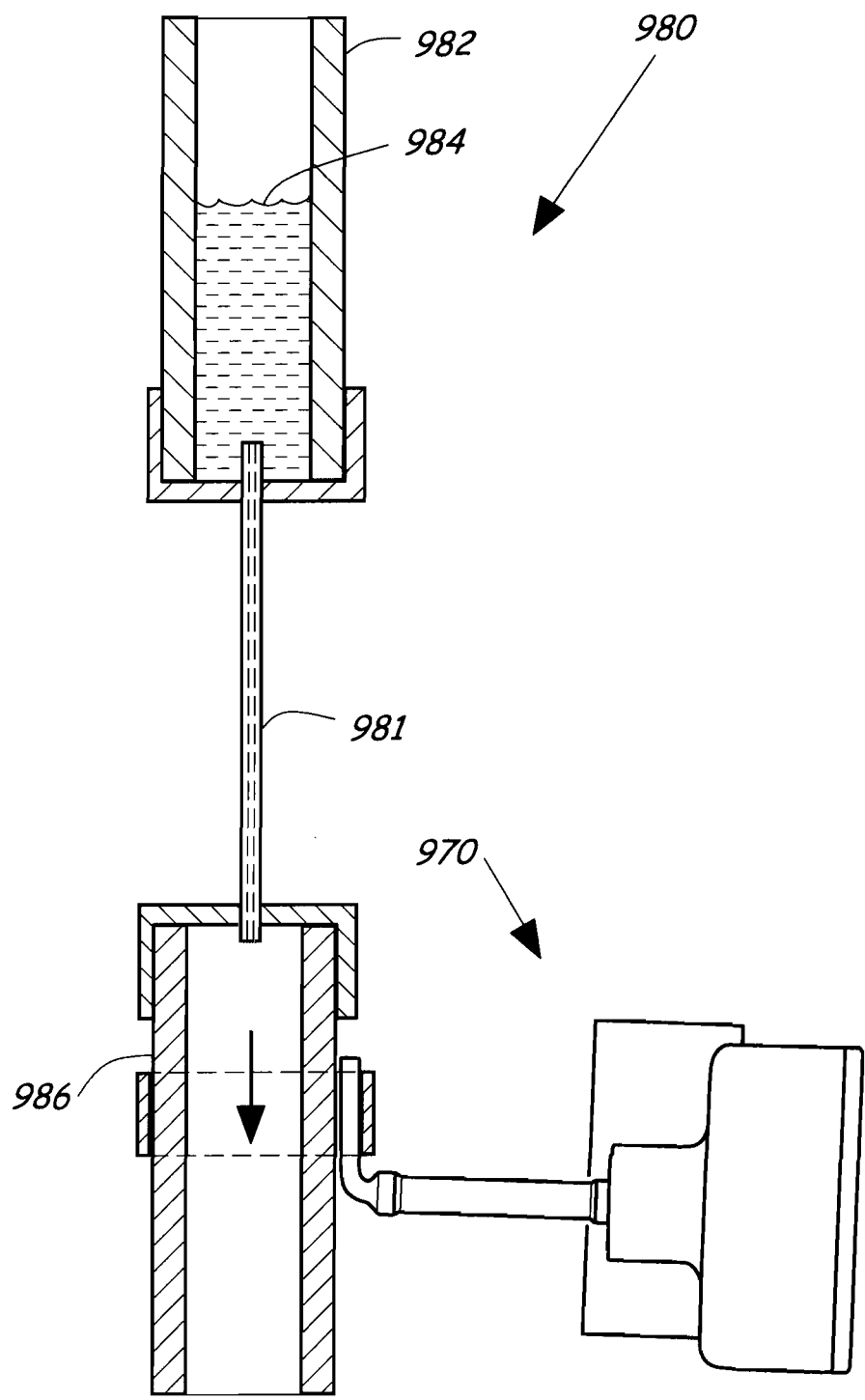
FIG. 13 illustrates a transducer assembly mounted to a flow control arrangement that includes a flow restriction.

FIG. 13 illustrates a transducer assembly 970 mounted to a flow control arrangement 980 that includes a flow restriction 981. According to one aspect, a high pressure side of process cooling system provide liquid refrigerant 984 to a flow restriction 981 that comprises a capillary tube as illustrated. As the liquid refrigerant 984 flows along the flow restriction 981 toward a low pressure side 986 of the process cooling system, the pressure of the liquid refrigerant 984 drops, and the refrigerant vaporizes into a gas as it exits the flow restriction 981 into the low pressure side 986, providing cooling. In the event that the process cooling system leaks refrigerant, and gas is flowing through the flow restriction 981 instead of liquid, acoustic noise is generated. According to one aspect, the transducer assembly 970 senses the associated acoustic noise and diagnoses the loss of refrigerant. According to another aspect, in the event the flow restrictor 981 is plugged, the normal noise associated with liquid flow is lost, and the transducer assembly 970 diagnoses plugging of the flow restriction 981.

Various aspects shown in the FIGS. 1-13 can be appropriately combined. According to one embodiment, the acoustic sensor 202 includes a piezoelectric element that includes a piezoelectric crystal disc that is mounted in a metal can with a force sensitive surface of the piezoelectric crystal disc facing the spring 204A as illustrated. The piezoelectric crystal disc acts as a diaphragm and receives sound from the spring 204A, the surrounding air, or both. The compression of the spring 204A maintains contact between the spring 204A and the piezoelectric crystal disc. The acoustic sensor 202 and the spring 204A provide filtering of the acoustic signal. According to one embodiment, circuitry in the electronics assembly 324 is tuned to a resonant frequency range of filtering provided by the spring 204A and the acoustic sensor 202. While a coil spring is illustrated in FIGS. 2-4, it will be understood by those skilled in the art that other shapes such as the shaft shown in FIG. 10 can be used to conduct acoustic signals and maintain contact with an acoustic sensor element.

It is to be understood that even though numerous aspects of various embodiments of the invention have been set forth in the foregoing description, this disclosure is illustrative only, and changes may be made in form and detail, without departing from the scope and spirit of the present invention. The present invention is not limited to the specific transducer assemblies shown herein and is applicable to other transducer assemblies as well as other pressure vessels.

What is claimed is:

1. A transducer assembly for diagnosing acoustic noise from a pressure vessel, comprising:
    an acoustic sensor element;
    an acoustic waveguide including a rotatable acoustic coupler coupled to the acoustic sensor element, a tube having a first tube end coupled to the rotatable acoustic coupler and a second tube end coupled to a foot portion which extends parallel with a sealed fluid conduit acoustically couplable to the sealed fluid conduit, wherein the foot portion extends parallel with the sealed fluid conduit along an exterior of the sealed fluid conduit; and
    a temperature sensor in the foot portion configured to sense a temperature of the conduit;
    a circuit assembly coupled to the acoustic sensor element and the temperature sensor, the circuit providing a diagnostic output responsive to an acoustic vibration delivered to the acoustic sensor element through the rotatable acoustic coupler and a temperature output from the temperature sensor, wherein the circuit assembly is rotatable about the rotatable acoustic coupler with respect to the foot portion.

2. The transducer assembly of claim 1 wherein the second tube end has an internal thermowell cavity adjacent the fluid conduit, and the temperature sensor is carried in the internal thermowell cavity and has an output cable that extends through the tube and the first tube end to the circuit assembly.

3. The transducer assembly of claim 2 wherein the temperature sensor is selected from the group of a thermistor and a thermocouple junction.

4. The transducer assembly of claim 1 wherein the circuit assembly provides static temperature compensation.

5. The transducer assembly of claim 1 wherein the circuit assembly provides dynamic temperature compensation.

6. The transducer assembly of claim 1 and further comprising:
    an electronic housing that is rotatable relative to the acoustic waveguide; and
    an electronic data display that is disposed on the electronic housing and that is aimable by rotation of the electronic housing.

7. The transducer assembly of claim 6 and further comprising frustoconical surfaces on the electronic housing and on the acoustic waveguide, the frustoconical surfaces being rotatable relative to one another.

8. The transducer assembly of claim 7 and further comprising a spring washer that compresses the frustoconical surfaces to control torque as the frustoconical surfaces are rotated relative to one another.

9. The transducer assembly of claim 1 wherein the acoustic sensor element is selected from the group of a piezoelectric force sensor, a capacitive force sensor and a magnetic force sensor.

10. The transducer assembly of claim 1, wherein the acoustic waveguide couples an acoustic vibration from a mounting surface of the foot portion to the acoustic sensor element through the rotatable acoustic coupler.

11. The transducer assembly of claim 10 wherein the acoustic vibration is in the range of 30 kHz to 50 kHz.

12. The transducer assembly of claim 10 further comprising an insulating cap that couples the acoustic vibration from the rotatable acoustic coupler to the acoustic sensor element, the insulating cap providing a rotatable joint between the rotatable acoustic coupler and the acoustic sensor element.

13. The transducer assembly of claim 12, wherein the rotatable acoustic coupler exerts a force on the acoustic sensor element through the insulating cap.

14. The transducer assembly of claim 13, wherein the acoustic sensor element comprises a spring, and compression of the spring presses the insulating cap against the acoustic sensor element.

15. The transducer assembly of claim 10, wherein the second tube end includes a bend that forms the foot portion, and the foot portion is configured to be mounted to the fluid conduit and extend parallel with the fluid conduit.

16. The transducer assembly of claim 1 and further comprising an electronic housing mounting flange that is mounted to the tube and that includes a threaded flange portion adjacent the first tube end.

17. The transducer assembly of claim 16 and further comprising an acoustic sensor support adapter that supports the acoustic sensor element and that includes a threaded support end that engages the threaded flange portion.

18. The transducer assembly of claim 1 wherein the tube comprises a metal tube having an external diameter of less than 11 millimeters.

19. The transducer assembly of claim 18 wherein the tube comprises a tube wall thickness of less than 2.0 millimeter.

20. A method of sensing acoustic energy at a fluid conduit, comprising:
    providing an acoustic sensor element;
    coupling a first end of a rotatable acoustic coupler to the acoustic sensor element;
    coupling a first end of a tube to a second end of the rotatable acoustic coupler;
    mounting a foot portion coupled to a second end of the tube to the fluid conduit; the foot portion extending parallel with the fluid conduit, wherein the foot portion extends parallel with the sealed fluid conduit along an exterior of the sealed fluid conduit;
    delivering an acoustic vibration from a mounting surface of the foot portion to the acoustic sensor element through the foot portion, the tube, and the rotatable acoustic coupler;
    sensing a temperature of the fluid conduit with a temperature sensor in the foot portion configured to thermally couple to the conduit;
    providing a first electrical output representative of the acoustic vibration using the acoustic sensor element
    diagnosing a condition of the fluid conduit based upon the first electrical output and the sensed temperature with an electrical circuit; and
    rotating the electrical circuitry about the rotatable acoustic coupler to a desired position with respect to the foot portion.

21. The method of claim 20, and further comprising:
    shaping the foot to include an internal thermowell cavity adjacent the mounting surface; and
    sensing a temperature in the internal thermowell cavity and providing a second electrical output representative of temperature.

22. The method of claim 20 and sensing the acoustic vibration with the acoustic sensor element in the range of 30 kHz to 50 kHz.

23. The method of claim 20 and coupling the rotatable acoustic coupler to the acoustic sensor element through an insulating cap that forms a rotatable joint between the rotatable acoustic coupler and the acoustic sensor element.

24. The method of claim 23 and exerting a force on the acoustic sensor element through the insulating cap using the rotatable acoustic coupler.

25. The method of claim 24, wherein the acoustic sensor element comprises a spring, and exerting a force on the acoustic sensor element through the insulating cap using the rotatable acoustic coupler comprises compressing the spring against the insulating cap.

26. The method of claim 20 and mounting the acoustic sensor element to an acoustic mounting flange and threading the mounting flange.

27. The method of claim 26 and mounting an electronics housing support adapter that includes a threaded end that engages the threading of the mounting flange.

28. The method of claim 20 and forming the tube of metal.

29. The method of claim 20 and bending a second end of the tube to form the foot portion.

* * * * *